(12) United States Patent
Aotsuka

(10) Patent No.: US 6,838,266 B2
(45) Date of Patent: Jan. 4, 2005

(54) METHOD FOR PRODUCING DNA

(75) Inventor: Satoshi Aotsuka, Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 67 days.

(21) Appl. No.: 09/917,330

(22) Filed: Jul. 27, 2001

(65) Prior Publication Data
US 2002/0034791 A1 Mar. 21, 2002

(30) Foreign Application Priority Data
Jul. 28, 2000 (JP) .......................................... 2000-229284

(51) Int. Cl.$^7$ ........................... C12P 19/34; C12Q 1/68; C07H 21/04; G01N 33/48
(52) U.S. Cl. ....................... 435/91.2; 435/6; 536/24.33; 702/19
(58) Field of Search .................. 435/6, 91.2; 536/24.33; 702/19, 101

(56) References Cited

FOREIGN PATENT DOCUMENTS

| WO | 94/10315 | 5/1994 |
|---|---|---|
| WO | 99/16904 | 4/1999 |

OTHER PUBLICATIONS

Sandhu et al. Dual Asymmetric PCR: One–Step Construction of Synthetic Genes. BioTechniques. 1992, vol. 12, No. 1, pp. 14–16.*

Chrisotomos Prodromou and Laurence H. Pearl, Recursive PCR: a novel technique for total gene synthesis, Oxford University Press, 1992, pp827–829.

Willem P.C.Stemmer, Andreas Crameri, Kim D.Ha, Thomas M.Brennan and Herbert L.Heyneker, Single–step assembly of a gene and entire plasmid from large numbers of oligodeoxyribonucleotides, Gene 164, 1995 pp49–53.

Horton, et al. "Engineering Hybrid Genes Without the Use of Restriction Enzymes: Gene Splicing by Overlap Extension," *Gene*, vol. 77, pp. 81–88, 1989.

Sandhu, et al. "Dual Asymmetric PCR: One–Step Construction of Synthetic Genes," *BioTechniques*, vol. 12, No. 1, pp. 14–16, 1992.

White, et al. "Concatemer Chain Reaction: A Taq DNA Polymerase–mediated Mechanism for Generating Long Tandemly Repetitive DNA Sequences," *Analytical Biochemistry*, vol. 199, pp. 184–190, 1991.

Ye, et al. "Gene Synthesis and Expression in *E. coli* for Pump. A Human Matrix Metalloproteinase," *Biochemical and Biophysical Research Communicationsl, vol. 186, No. 1, pp. 143–149, 1992.*

European Search Report completed Dec. 4, 2003 and issued in a related pending foreign application.

* cited by examiner

*Primary Examiner*—Marjorie Moran
*Assistant Examiner*—Lori A. Chow
(74) *Attorney, Agent, or Firm*—Knobbe, Martens, Olson & Bear, LLP

(57) ABSTRACT

DNA is produced by preparing oligomers having partial sequences selected according to a specific scheme based on a target nucleotide sequence, and performing PCR using two of single strand DNAs base-paired at their 3' ends as primers and templates to prepare DNA, in a specific manner.

1 Claim, 3 Drawing Sheets

SEQUENCE LISTING

<160> NUMBER OF SEQ ID NOS: 22

<210> SEQ ID NO 1
<211> LENGTH: 630
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 1
ggctcgaggt accgcggccg ctcacaagac aaggcaacca gattttttct tcccacgtct      60
agcttgcaga gcagctctcg tagccatttc aaaaacctct ctcactccat ctttggtctt     120
tgctgaacac tccatgtacc caaaagcgcc aatcctgttt gccatatctc tgccttcttc     180
aggtttcacc ggctcctgct tcatcttggc tagctcccgc cttgtgtgct catcattccg     240
aagatccttc ttattcccaa cccggatgat gggcacgttg ggacagaaat gcttgacttc     300
tggggtccac ttttctggga tgttttctaa actatcaggg ctgtcgatgg aaaaacacat     360
cagtataaca tcggtatctg ggtaggagag gggcctcagg cgatcataat cttcctgccc     420
agctgtgtcc cacaaagcca actctacctg cttcccatcc acctcgatat ctgccacata     480
gttctcaaac actgtgggca catacacctc tgggaactgg tccttgctga agactattaa     540
taggcatgtc tttccacagg ctacatcacc aacaatcacc agtttcttcc ggttcaggtc     600
ctcctcggag atcagcttct gctccatggg                                      630

<210> SEQ ID NO 2
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 2
aagatccttc ttattcccaa ccaggatgat gggcacgttg ggacagaaat gcttgacttc      60
tggggtccac ttttctggga tgttttctaa                                       90

<210> SEQ ID NO 3
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 3
aggtttcacc ggctcctgct tcatcttggc tagctcccgc cttgtgtgct catcattccg      60
aagatccttc ttattcccaa ccaggatgat                                       90

<210> SEQ ID NO 4
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4
tgctgaacac tccatgtacc caaaagcgcc aatcctgttt gccatatctc tgccttcttc      60
aggtttcacc ggctcctgct tcatcttggc                                              90

<210> SEQ ID NO 5
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
agcttgcaga gcagctctcg tagccatttc aaaaacctct ctcactccat ctttggtctt              60
tgctgaacac tccatgtacc caaaagcgcc                                              90

<210> SEQ ID NO 6
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6
ggctcgaggt accgcggccg ctcacaagac aaggcaacca gatttttct tcccacgtct              60 agcttgcaga gcagctctcg tagccatttc                                              90

<210> SEQ ID NO 7
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
ctctcctacc cagataccga tgttatactg atgtgttttt ccatcgacag ccctgatagt              60
ttagaaaaca tcccagaaaa gtggacccca                                              90

<210> SEQ ID NO 8
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 8
caggtagagt tggctttgtg ggacacagct gggcaggaag attatgatcg cctgaggccc              60
ctctcctacc cagataccga tgttatactg                                              90

<210> SEQ ID NO 9
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 9
gaggtgtatg tgcccacagt gtttgagaac tatgtggcag atatcgaggt ggatggaaag              60
caggtagagt tggctttgtg ggacacagct                                              90

```
<210> SEQ ID NO 10
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 10
ggtgatgtag cctgtggaaa gacatgccta ttaatagtct tcagcaagga ccagttccca     60
gaggtgtatg tgcccacagt gtttgagaac                                      90

<210> SEQ ID NO 11
<211> LENGTH: 90
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 11
cccatggagc agaagctgat ctccgaggag gacctgaacc ggaagaaact ggtgattgtt     60
ggtgatgtag cctgtggaaa gacatgccta                                      90

<210> SEQ ID NO 12
<211> LENGTH: 612
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 12
attaagaaac atgtagaatt aggttttcca ccaacaagct ttgtaccect tgatgtaaag     60 aaccgtaaac aacacgttgc tttgcttatg aattcttctg gatctactgg tttacctaaa   120
ggtgtacgaa ttacccacga aggtgcagtt acaagattct cacacgctaa ggatccaatt   180
tacgaaaacc aagtttcacc tggtactgct attttaactg tcgttccgtt ccatcatgga   240
tttggaatgt ttaccacttt aggatacttt gcttgcggat accgtgttgt aatgttaaca   300
aaatttgatg aagaactgtt tttgagaact ttgcaagatt ataagtgtac cagtgtgatt   360
cttgtaccaa ccttatttgc tattctcaac aagagtgaat tgatcgataa gttcgattta   420
tctaatctaa ctgaaattgc ttctggtgga gctcctttgg caaaagaagt tggcgaagca   480
gtcgctagaa gatttaatct acccggtgtc cgtcagggtt acggattaac agaaacaaca   540
tctgcattta ttattactcc agaaggtgat gataaacctg gagcatctgg aaaagtggta   600
cccttattca aa                                                         612

<210> SEQ ID NO 13
<211> LENGTH: 104
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 13
attaagaaac atgtagaatt aggttttcca ccaacaagct ttgtaccect tgatgtaaag     60 aaccgtaaac aacacgttgc tttgcttatg aattcttctg gatc                    104

<210> SEQ ID NO 14
```

<211> LENGTH: 104
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 14 ttggatccttt agcgtgtgag aatcttgtaa ctgcaccttc gtgggtaatt cgtacacctt      60
taggtaaacc agtagatcca gaagaattca taagcaaagc aacg                      104

<210> SEQ ID NO 15
<211> LENGTH: 104
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 15
ttacaagatt ctcacacgct aaggatccaa tttacggaaa ccaagtttca cctggtactg      60
ctattttaac tgtcgttccg ttccatcatg gatttggaat gttt                      104

<210> SEQ ID NO 16
<211> LENGTH: 104
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 16
ctcaaaaaca gttcttcatc aaattttgtt aacattacaa cacggtatcc gcaagcaaag      60
tatcctaaag tggtaaacat tccaaatcca tgatggaacg gaac                      104

<210> SEQ ID NO 17
<211> LENGTH: 104
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 17
ttgtaatgtt aacaaaattt gatgaagaac tgttttttgag aactttgcaa gattataagt     60
gtaccagtgt gattcttgta ccaaccttat ttgctattct caac                      104

<210> SEQ ID NO 18
<211> LENGTH: 104
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 18
tttgccaaag gagctccacc agaagcaatt tcagttagat tagataaatc gaacttatcg      60
atcaattcac tcttgttgag aatagcaaat aaggttggta caag                      104

-continued

```
<210> SEQ ID NO 19
<211> LENGTH: 104
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 19
aattgcttct ggtggagctc ctttggcaaa agaagttggc gaagcagtcg ctagaagatt      60
taatctaccc ggtgtccgtc agggttacgg attaacagaa acaa                     104

<210> SEQ ID NO 20
<211> LENGTH: 104
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 20
tttgaataag ggtaccactt ttccagatgc tccaggttta tcatcacctt ctggagtaat      60
aataaatgca gatgttgttt ctgttaatcc gtaaccctga cgga                     104

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 21
attaagaaac atgtagaatt                                                 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 22
tttgaataag ggtaccactt                                                 20
```

US 6,838,266 B2

METHOD FOR PRODUCING DNA

BACKGROUND OF THE INVENTION

The present invention relates to a method for producing DNA.

As methods for producing DNA, methods based on PCR, methods based on chemical synthesis reactions utilizing automatic synthesizers and so forth are known.

However, when production of DNA having an arbitrary nucleotide sequences is intended, a limitation that DNA having a desired nucleotide sequence should exist beforehand for use as a template, is imposed on the methods based on PCR. Further, in the methods based on chemical synthesis reactions, maximum length of practically producible DNA is limited and therefore production of DNA having a further longer length requires ligation reactions utilizing restriction enzymes and ligases, resulting in a limitation concerning the presence of restriction enzyme recognition sequences.

SUMMARY OF THE INVENTION

An object of the present invention is to provide a method for producing DNA having an arbitrary sequence, which is free from such limitations as mentioned above.

The inventor of the present invention found that DNA having an arbitrary nucleotide sequence can be synthesized without suffering from such limitations as described above by carrying out steps of preparing oligomers having partial sequences selected according to a specific scheme based on a target nucleotide sequence, and performing PCR using two of single strand DNAs base-paired at their 3' ends as primers and templates to prepare DNA, in a specific manner. Thus, the present invention has been accomplished.

The present invention provides a method for producing DNA, which comprises the following steps (1) to (4) (also referred to as the "first production method of the present invention" hereinafter):

(1) dividing a target sequence which is a nucleotide sequence of DNA to be synthesized into 2N wherein N is a positive integer, of sections, designing partial sequences each containing a nucleotide sequence of each section and a part of a nucleotide sequence of an adjacent section or parts of nucleotide sequences of adjacent sections, wherein the part or parts have such a length that the nucleotide sequence of the each part can specifically make base-pairing with a nucleotide sequence complementary thereto, and preparing oligomers each having each of the 1st to Nth partial sequences from the 5' end of the target sequence and oligomers each having a nucleotide sequence complementary to each of the (N+1)th to (2N)th partial sequences from the 5' end of the target sequence, (2) performing PCR by using an oligomer having the Nth partial sequence from the 5' end of the target sequence and an oligomer having a nucleotide sequence complementary to the (N+1)th partial sequence from the 5' end of the target sequence under such a condition that these oligomers should act as primers and templates, (3) sequencing synthesized DNAs and selecting DNA having a nucleotide sequence containing the Nth and (N+1)th partial sequences from the 5' end of the target sequence, and (4) repeating the following steps (4a) and (4b) for J wherein J is an integer, to be from 1 to N-1:

(4a) performing PCR by using the selected DNA, an oligomer having the (N−J)th partial sequence from the 5' end of the target sequence and an oligomer having a nucleotide sequence complementary to the (N+1+J)th partial sequence from the 5' end of the target sequence under such a condition that the DNA and oligomers should act as primers and templates, and (4b) sequencing synthesized DNAs and selecting DNA having a nucleotide sequence containing the (N−J)th to (N+1+J)th partial sequences.

The present invention further provides a method for producing DNA, which comprises the following steps (1) to (4) (also referred to as the "second production method of the present invention" hereinafter):

(1) dividing a target sequence which is a nucleotide sequence of DNA to be synthesized into $2^n$ wherein n is a positive integer, of sections, designing partial sequences each containing a nucleotide sequence of each section and a part of a nucleotide sequence of an adjacent section or parts of nucleotide sequences of adjacent sections, wherein the part or parts have such a length that the nucleotide sequence of each part can specifically make base-pairing with a nucleotide sequence complementary thereto, and preparing oligomers each having each of (odd number)th partial sequences from the 5' end of the target sequence and oligomers each having a nucleotide sequence complementary to each of (even number)th partial sequences from the 5' end of the target sequence, (2) repeating the following step (2a) for j wherein j is an integer, to be from 1 to $2^{n-1}$ to produce $2^{n-1}$ of reaction products, (2a) performing PCR by using an oligomer having the (2j−1)th partial sequence from the 5' end of the target sequence and an oligomer having a nucleotide sequence complementary to the (2j)th partial sequence from the 5' end of the target sequence under such a condition that these oligomers should act as primers and templates, (3) repeating the following step (3a) for i wherein i is an integer, to be from 2 to n:

(3a) repeating the following step (3ai) for k wherein k is an integer, to be from 1 to $2^{n-i}$ to produce $2^{n-i}$ of reaction products, (3ai) mixing a reaction mixture containing DNA having the ($2^i \cdot (k-1)+1$)th to ($2^i \cdot (k-\frac{1}{2})$)th partial sequences from the 5' end of the target sequence and a reaction mixture containing DNA having a sequence complementary to the ($2^i \cdot (k-\frac{1}{2})+1$)th to ($2^i \cdot k$)th partial sequences from the 5' end of the target sequence and performing PCR under such a condition that DNAs contained in the reaction mixtures should act as primers and templates, and (4) separating DNAs having a length expected from the target sequence from the reaction mixture, and sequencing the separated double strand DNAs to select a double strand DNA having the target sequence.

In the second production method of the present invention, a ratio of the oligomers added to the reaction mixture or a ratio of the reaction mixtures to be mixed is preferably adjusted so that a single strand DNA required for a subsequent step should be synthesized in an amount larger than that of the other single strand DNA in the steps (2a) and (3ai).

According to the present invention, there are provided novel methods for producing DNA. According to the first production method of the present invention, there can be practically produced DNA having a length several times larger than the maximum length that can practically be produced by the chemical synthesis method. Further, since restriction enzyme treatment is not essential during the production, the limitation imposed on producible DNA sequence is ameliorated. In addition, in the second production method of the present invention, a cloning step is not included as an intermediate step, and because lengths of the reaction products are approximately doubled in each step, it becomes easy to select the final product. Because of these, rapid and efficient production can be realized.

DETAILED DESCRIPTION OF THE INVENTION

Figure 1:
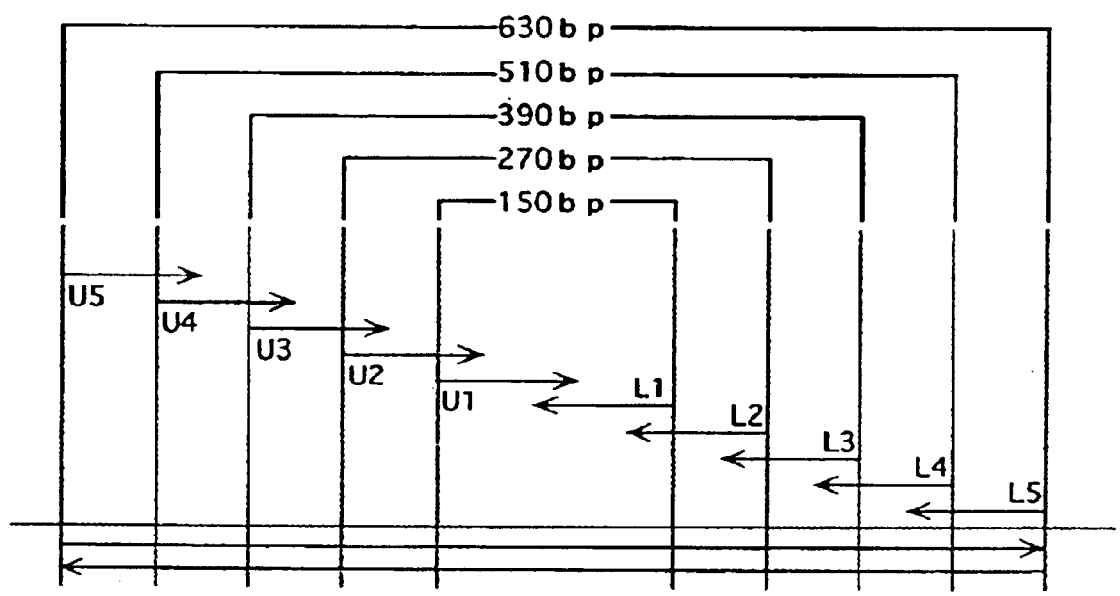
FIG. 1 shows positional relationship of oligomers in an example of the first production method of the present invention.

<First Production Method of the Present Invention>

The first production method of the present invention is characterized in that equal numbers of oligomers each having a partial sequence of a target sequence for about half of the 5' end side of the target sequence and oligomers each having a sequence complementary to a partial sequence of a target sequence for about half of the 3' end side of the target sequence are prepared so that the partial sequences should have overlaps with adjacent partial sequences, PCR is first performed by using the most internally located two oligomers as primers and templates, and then PCR is repeated by using a reaction product and oligomers located immediately outside the previous ones as primers and templates until the reaction product should have a length of the target sequence.

Each step of the first production method of the present invention will be explained.

In the step (1), a target sequence which is a nucleotide sequence of DNA to be synthesized is divided into 2N (N is a positive integer) of sections; partial sequences each containing a nucleotide sequence of each section and a part of a nucleotide sequence of an adjacent section or parts of nucleotide sequences of adjacent sections are designed, wherein the part or parts have such a length that the nucleotide sequence of the each part can specifically make base-pairing with a nucleotide sequence complementary thereto; and oligomers each having each of the 1st to Nth partial sequences from the 5' end of the target sequence and oligomers each having a nucleotide sequence complementary to each of the (N+1)th to (2N)th partial sequences from the 5' end of the target sequence are prepared. A terminal partial sequence has the part (overlap) only at the internal end, and an internal partial sequence has the parts at the both ends.

The oligomers having a partial sequence or a sequence complementary thereto designed in this step serve as primers and templates in PCR. Therefore, the term "specifically make base-pairing" means to specifically make base-pairing under the PCR conditions used in the steps (2) and (4a).

A longer partial sequence provides higher efficiency for middle steps. However, the maximum length of DNA practically synthesized by chemical synthesis is limited. Therefore, the length of the partial sequence is usually 150 nucleotides or less, and it is preferably 80–120 nucleotides, if yield, synthesis efficiency and so forth are taken into consideration. In theory, the length of the target sequence is not limited except for a case where the sequence contains repeating sequences. However, if it is taken into consideration that the target sequence is selected by sequence analysis, it is preferably a length that can be determined by once of sequence analysis, and it is usually 1000 nucleotides or less. The number of N is determined based on the lengths of the target sequence and partial sequences as well as overlapping lengths of nucleotide sequences of adjacent sections in the partial sequences.

The overlapping length of nucleotide sequences in partial sequences for adjacent sections may be a length sufficient for the specific base-pairing, and it is usually 17–40 nucleotides. The sequence of the overlap is selected so that, under the conditions of PCR, formation of primer dimers due to base-pairing at unintended position, intramolecular base-pairing of primer and so forth should be prevented and a suitable denaturation temperature (GC content) should be obtained, as is taken into consideration in the design of primer for usual PCR. All of the lengths of the partial sequences or the overlaps may not be in an equal length, and they may be suitably selected considering the target sequence and the above factors.

In the step (2), PCR is performed by using an oligomer having the Nth partial sequence from the 5' end of the target sequence and an oligomer having a nucleotide sequence complementary to the (N+1)th partial sequence from the 5' end of the target sequence under such a condition that these oligomers should act as primers and templates.

In PCR performed in this step, two kinds of oligomers serve as both of primers and templates, and primers and templates are not distinguished. That is, two kinds of oligomers are base-paired at their 3' ends, and act as both of primers and templates during the extension of each strand.

That is, an oligomer having the Nth partial sequence from the 5' end of the target sequence and an oligomer having a nucleotide sequence complementary to the (N+1)th partial sequence from the 5' end of the target sequence are added to a reaction mixture where extension reaction by DNA polymerase can be caused, and denaturation reaction, annealing reaction and extension reaction are repeated to synthesize DNA.

The conditions for PCR can be determined by considering factors similar to those of usual PCR.

A typical example of the PCR reaction mixture is a mixture containing 0.5 µM each of oligomers, 20 mM of Tris-HCl (pH 8.3 (25° C.)), 1.5 mM of $MgCl_2$, 0.05% of Tween 20, 100 µg/ml of gelatin or BSA, 50 µM each of dNTP and 0.02 units/µl of Taq DNA polymerase (concentrations are final concentrations). The thermal cycle for the reactions may consist of, for example, a cycle of 94–98° C. for 30 seconds to 1 minute for denaturation, 50–60° C. for 30 seconds to 1 minute for annealing, and 65–72° C. for 30 seconds to 1 minute for extension, which is repeated 20 to 30 times, and extension of the final extension reaction for 5 to 10 minutes. Before the cycle, the denaturation reaction may be performed for 2–5 minutes. The reaction is usually stopped by cooling the mixture to 4° C. and addition of EDTA (final concentration: 10 mM).

Concentration of dNTP is usually 0.1–0.5 µM. The concentration of dNTP is determined by considering yield of reaction products, specificity of base-pairing, accuracy of polymerization and so forth.

Magnesium concentration is usually 1.5–3.5 mM. The $Mg^{2+}$ concentration is determined by considering EDTA concentration in the reaction mixture, annealing of primers, denaturation temperature of DNA, specificity of reaction, formation of primer dimer, enzyme activity, accuracy of polymerization and so forth.

Concentration of the primer (oligomer) is usually 0.1–0.5 µM. When the concentration is too high, the specificity of reaction may be reduced, and primer dimer and so forth may be formed.

While concentration of DNA polymerase may vary depending on the type of the polymerase, in case of Taq DNA polymerase, it is usually 1–4 units/100 μl. If the amount of the enzyme is too large, non-specific amplification may occur.

In the first cycle of PCR performed in this step, two kinds of oligomers base-paired at their 3' ends serve as primers and templates, and in the second cycle and thereafter, DNA produced by the extension reaction may be involved in the reaction as a template. That is, there also may occur a reaction in which DNA produced by the extension reaction acts as a template and the oligomers as a whole act as only primer. Therefore, the denaturation conditions are usually determined so that sufficient denaturation of the DNA that can be a template should be obtained.

The conditions for annealing are determined by considering denaturation temperature, length and concentration of primer and so forth. The temperature is usually, for example, a temperature lower than the denaturation temperature of primer by about 5° C.

The conditions for extension are determined by considering the type of DNA polymerase to be used, length and amount of a portion desired to be extended and temperature. When Taq DNA polymerase is used as the DNA polymerase, the temperature may be its optimal temperature. Since DNA polymerase may be inactivated depending on the denaturation conditions, supplemental addition of DNA polymerase is also taken into consideration.

The above-described PCR can be performed by using widely used apparatuses and enzymes for PCR and so forth as they are.

Further, in such PCR as described above, since DNA used as a template is a single strand DNA, non-specific base-pairing and extension reaction may occur before the temperature reaches the first denaturation temperature, thereby causing non-specific amplification. In such a case, a technique called hot start method may be used, in which the reaction does not occur until the temperature reaches the first denaturation temperature, and it only occurs after the temperature reaches a predetermined temperature.

In the step (3), the synthesized DNAs are sequenced and DNA having a nucleotide sequence containing the Nth and (N+1)th partial sequences from the 5' end of the target sequence is selected.

The sequencing of the synthesized DNAs can be performed in a conventional manner. For example, reaction products obtained in the step (2) are subjected to agarose gel electrophoresis, and DNAs having an expected length are extracted from the gel, cloned into a suitable vector, and sequenced. DNA containing the Nth and the (N+1)th partial sequences from the 5' end of the target sequence may be selected and used in the form of the vector as a template in a subsequent reaction.

In the step (4), the following steps (4a) and (4b) are repeated for J (J is an integer) to be from 1 to N−1.

(4a) PCR is performed by using the selected DNA, an oligomer having the (N−J)th partial sequence from the 5' end of the target sequence and an oligomer having a nucleotide sequence complementary to the (N+1+J)th partial sequence from the 5' end of the target sequence.

(4b) The synthesized DNAs are sequenced and DNA having a nucleotide sequence containing the (N−J)th to (N+1+J)th partial sequences is selected.

In PCR performed in the step (4a), each single strand of DNA and two kinds of oligomers serve as both of primers and templates, and primers and templates are not distinguished. That is, one single strand and one oligomer and the other single strand and the other oligomer are base-paired at their 3' ends, respectively, and act as both of primers and templates during the extension of each strand.

That is, the selected DNA, an oligomer having the (N−J)th partial sequence from the 5' end of the target sequence and an oligomer having a nucleotide sequence complementary to the (N+1+J)th partial sequence from the 5' end of the target sequence are added to a reaction mixture where extension reaction by DNA polymerase can be caused, and denaturation reaction, annealing reaction and extension reaction are repeated to synthesize DNA.

The step (4a) can be performed in the same manner as the step (2) except that a selected DNA is further contained and different oligomers are used. The conditions of PCR are determined by taking these differences into consideration. However, if the conditions for the step (2) are determined with taking the conditions of the step (4a) into consideration, it can be performed with the same conditions as the step (2).

The step (4b) may be performed in the same manner as the step (3).

Hereafter, the method will be explained with reference to an example where DNA having a nucleotide sequence of 630 nucleotides in length is produced.

The total length is divided into 10 sections (N=5), and partial sequences are determined with a partial sequence length of 90 nucleotides and an overlap length of 30 nucleotides (FIG. 1). Then, oligomers (U5 to U1) each having each of the first to fifth partial sequences from the 5' end and oligomers (L1 to L5) each having a nucleotide sequence complementary to each of the sixth to tenth partial sequences are synthesized.

By using oligomers U1 and L1, PCR is performed with conditions of 94° C. for 2 minutes, subsequent repetition of a cycle of 98° C. for 30 seconds, 60° C. for 30 seconds and 68° C. for 1 minute for 30 times, and 68° C. for 10 minutes to synthesize DNA of 150 nucleotides. The obtained DNAs are sequenced, and DNA having an intended sequence is selected.

Then, the following steps (I) to (IV) are performed.

(I) PCR is performed under the same conditions as mentioned above by using the selected DNA and the oligomers U2 and L2 to synthesize DNA of 270 bp. The obtained DNAs are sequenced, and DNA having an intended sequence is selected.

(II) PCR is performed under the same conditions as mentioned above by using the selected DNA and the oligomers U3 and L3 to synthesize DNA of 390 bp. The obtained DNAs are sequenced, and DNA having an intended sequence is selected.

(III) PCR is performed under the same conditions as mentioned above by using the selected DNA and the oligomers U4 and L4 to synthesize DNA of 510 bp. The obtained DNAs are sequenced, and DNA having an intended sequence is selected.

(IV) PCR is performed under the same conditions as mentioned above by using the selected DNA and the oligomers U5 and L5 to synthesize DNA of 630 bp. The obtained DNAs are sequenced, and DNA having an intended sequence is selected.

In this way, by ligating DNAs obtained through a chemical synthesis method, there can be produced DNA several times longer than the maximum length that can be practically obtained by the chemical synthesis method. And since restriction enzyme treatment is not essential for this method as middle steps, DNA having an arbitrary sequence can be produced.

<Second Production Method of the Present Invention>

The second production method of the present invention is characterized in that equal numbers of oligomers each having a partial sequence of a target sequence and oligomers each having a sequence complementary to a partial sequence of a target sequence are prepared, wherein the former and latter partial sequences are in an alternate positional relationship, so that the partial sequences should have overlaps with adjacent partial sequences; PCR is first performed by using each pair of adjacent oligomers as primers and templates; and then PCR is repeated by using each pair of adjacent reaction products as primers and templates until a reaction product should have a length of the target sequence.

Each step of the second production method of the present invention will be explained.

In the step (1), a target sequence which is a nucleotide sequence of DNA to be synthesized is divided into $2^n$ (n is a positive integer) of sections; partial sequences each containing a nucleotide sequence of each section and a part of a nucleotide sequence of an adjacent section or parts of nucleotide sequences of adjacent sections are designed, wherein the part or parts have such a length that the nucleotide sequence of each part can specifically make base-pairing with a nucleotide sequence complementary thereto; and oligomers each having each of (odd number)th partial sequences from the 5' end of the target sequence and oligomers each having a nucleotide sequence complementary to each of (even number)th partial sequences from the 5' end of the target sequence are prepared. A terminal partial sequence has the part (overlap) only at the internal end, and an internal partial sequence has the parts at the both ends.

The oligomers having a partial sequence or a sequence complementary thereto determined in this step are used as primers and templates in PCR. Therefore, the term "specifically make base-pairing" means to specifically make base-pairing under the PCR conditions used in the steps (2a) and (3ai).

Length of the partial sequence may be a length of DNA that can practically produced by chemical synthesis, and it is usually 80–120 nucleotides. The number of n is determined based on this length, the length of the target sequence, accuracy of polymerization and so forth, and it is usually 2–4. If it exceeds this range, it may become likely that mutations are introduced, and thus it may become unlikely that a target sequence can be obtained.

The overlapping length of nucleotide sequences of adjacent sections in the partial sequences may be a length sufficient for the specific base-pairing, and it is usually 17–40 nucleotides. The sequence of the overlap is selected so that, under the conditions of PCR, formation of primer dimers due to base-pairing at unintended position, intramolecular base-pairing of primer and so forth should be prevented and a suitable denaturation temperature (GC content) should be obtained, as is taken into consideration in the design of primer for usual PCR. All of the lengths of the partial sequences or the overlaps may not be in an equal length, and they may be suitably selected considering the target sequence and the above factors. For example, since the length of DNA serving as a primer and a template becomes longer as the reaction steps proceed, the length of the overlap may be changed taking it into consideration.

In the step (2), the following step (2a) is repeated for j (j is an integer) to be from 1 to $2^{n-1}$ to produce $2^{n-1}$ of reaction products.

(2a) PCR is performed by using an oligomer having the (2j−1)th partial sequence from the 5' end of the target sequence and an oligomer having a nucleotide sequence complementary to the (2j)th partial sequence from the 5' end of the target sequence under such a condition that these oligomers should act as primers and templates.

The step (2a) can be performed in the same manner as the step (2) of the first production method of the present invention. However, the conditions are preferably determined by considering the DNA used in the step (3ai) as primers and templates. Further, EDTA is not added to stop the reaction.

In the step (3), the following step (3a) is repeated for i (i is an integer) to be from 2 to n.

(3a) The following step (3ai) is repeated for k (k is an integer) to be from 1 to $2^{n-i}$ to produce $2^{n-i}$ of reaction products.

(3ai) A reaction mixture containing DNA having the ($2^i \cdot (k-1)+1$)th to ($2^i \cdot (k-\frac{1}{2})$)th partial sequences from the 5' end of the target sequence and a reaction mixture containing DNA having a sequence complementary to the $2^i \cdot (k-\frac{1}{2})+1$)th to ($2^i \cdot k$)th partial sequences from the 5' end of the target sequence are mixed and PCR is performed under such a condition that DNAs contained in the reaction mixtures should act as primers and templates.

In the step (3ai), reaction mixtures obtained in a preceding step are mixed to perform PCR. While the reaction conditions for denaturation, annealing, and extension may be the same as those of the step (2a), conditions for a part or all of denaturation, annealing, and extension may be changed depending on the extended length of DNA that serves as primers and templates. Further, depending on the conditions of PCR, other reagents such as DNA polymerase may be added upon mixing of the reaction mixtures.

In the step (4), DNAs having a length expected from the target sequence are separated, and the separated double-strand DNAs are sequenced to select a double-strand DNA having the target sequence.

The separation and sequencing of DNA in the step (4) may be performed in the same manner as the step (3) of the first production method of the present invention.

Hereafter, the method will be explained with reference to an example where DNA having a nucleotide sequence of 500 nucleotides in length is produced.

Figure 2:
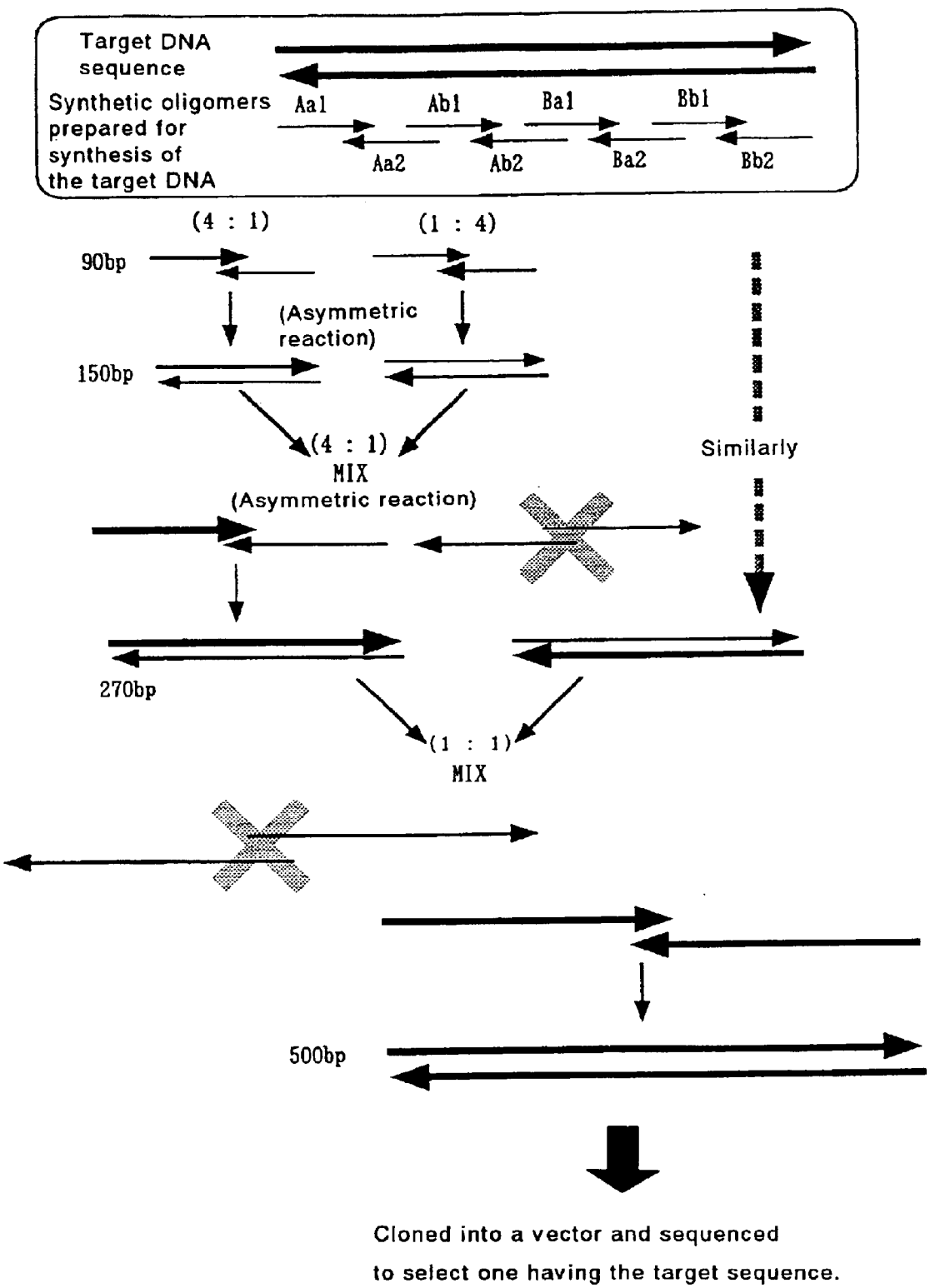
FIG. 2 shows positional relationship of oligomers in an example of the second production method of the present invention and outline of the process.

As shown in the frame in FIG. 2, eight (n=3) of oligomers (length: 90 nucleotides), Aa1, Aa2, Ab1, Ab2, Ba1, Ba2, Bb1 and Bb2, are prepared. They are designed so that Aa1 and Aa2, Ab1 and Ab2, Ba1 and Ba2, Bb1 and Bb2, Aa2 and Ab1, and Ba2 and Bb1 should overlap for 30 nucleotides, respectively, and Ab2 and Ba1 should overlap for 40 nucleotides.

First, reaction mixtures containing Aa1 and Aa2, Ab1 and Ab2, Ba1 and Ba2, and Bb1 and Bb2, respectively, are prepared, and PCR is performed for each mixture. After the reaction, the reaction mixture of Aa and the reaction mixture of Ab, and the reaction mixture of Ba and the reaction mixture of Bb are mixed respectively, and PCR is performed for each mixture. After the second reaction, the reaction mixtures obtained after the second reaction are mixed, and PCR is performed. The obtained reaction products are subjected to agarose gel electrophoresis, and DNAs having an expected length are extracted from the gel, cloned into a suitable vector, and sequenced to select a clone of the target sequence.

In the second production method of the present invention, a further longer DNA can be synthesized by increasing the number of steps of the mixing of reaction-products. However, it becomes likely that mutations are introduced, and thus it becomes unlikely that DNA having a target sequence can be obtained. By sequencing DNA of about 500 nucleotides once when it is synthesized, and by using it according to other methods, a further longer final product can be produced.

By the second production method of the present invention, DNA having an arbitrary sequence can also be produced, because restriction enzyme treatment is not essential for this method as middle steps like the first production method of the present invention.

Uncompleted oligomers such as those having a shorter 5'-end-side sequence due to stop of the reaction in their synthesis cycle are not likely to be involved in a reaction in a subsequent step, because they have only a short or no portion for annealing, and thus it is unlikely that clones having deletion should be synthesized. Therefore, the oligomers can be used even with a low purification degree.

Since the length of the reaction product is approximately doubled in every step, the final reaction product shows significant difference in length with respect to other products (e.g., those undergone only reactions of previous steps), and hence it can be easily collected from the gel.

In the second production method of the present invention, a ratio of the oligomers added to the reaction mixture or a ratio of reaction mixtures are preferably adjusted so that a single strand DNA required for a subsequent step should be synthesized in an amount larger than that of the other single strand DNA in the steps (2a) and (3ai).

A single strand DNA required for a subsequent step is synthesized in an amount larger than that of the other single strand DNA by changing the ratio of the initial amounts of oligomers and the ratios of amounts of the reaction mixtures mixed except for the last mixing of the reaction mixtures, as in the asymmetric PCR (e.g., 1:2–1:9).

A case where the ratio is 1:4 will be explained with reference to FIG. 2. PCR is performed by adding Aa1 and Aa2 in an amount ratio of 4:1, Ab1 and Ab2 in a ratio of 1:4, Ba1 and Ba2 in a ratio of 4:1, and Bb1 and Bb2 in a ratio of 1:4 to a reaction mixture (Ba1 and Ba2, and Bb1 and Bb2 are not shown in the figure). Then, PCR is performed by mixing the reaction mixture of Aa1 and Aa2 and the reaction mixture of Ab1 and Ab2 in a ratio of 4:1. PCR is also performed by mixing the reaction mixture of Ba1 and Ba2 and the reaction mixture of Bb1 and Bb2 in a ratio of 1:4 (not shown in the figure). Subsequently, PCR is performed by mixing the reaction mixture of Aa1 to Ab2 and the reaction mixture of Ba1 to Bb2 in a ratio of 1:1. The obtained reaction products are subjected to agarose gel electrophoresis, and DNAs having an expected length are extracted from the gel, cloned into a suitable vector, and sequenced to select a clone of the target sequence.

In the second production method of the present invention, the 3' end portion not required to be extended may be modified so that it should not be extended to improve the synthesis efficiency of the target product. While examples of such modification of 3' end include amination, biotinylation, digoxigenylation and so forth, amination that is a small modification in terms of the molecular size is preferred in order not to affect Tm so much.

In the second production method of the present invention, primers of about 20-mer may be designed for the both ends of the synthesized final product and PCR may be performed by using this final product as a template. In this way, the amount of the final product obtained in a small amount may be increased, and products having deletion at the one or both ends may be excluded.

EXAMPLES

Hereafter, the present invention will be explained with reference to the following examples.

EXAMPLE 1

In order to synthesize DNA having the nucleotide sequence shown in SEQ ID NO: 1 (target sequence), the target sequence was divided into ten sections, and partial sequences of the target sequence were designed with a length of 90 nucleotides and overlap of adjacent sections of 30 nucleotides. Further, oligomers each having each of the partial sequences of the target sequence (U1 to U5) and oligomers each having a sequence complementary to each of the partial sequences of the target sequence (L1 to L5) were synthesized. The nucleotide sequences of U1 to U5 and L1 to L5 are shown in SEQ ID NOS: 2–11, respectively. The positional relationship of U1 to U5 and L1 to L5 is shown in FIG. 1.

For reaction, 25 $\mu$l of a reaction mixture containing 0.4 $\mu$M each of U1 and L1, 40 mM of Tricine-KOH (pH 9.2 at 25° C.), 15 mM of potassium acetate (KOAc), 1.5 mM of magnesium acetate (Mg(OAc)$_2$), 75 $\mu$g/ml of bovine serum albumin (BSA) and 0.2 mM each of dNTP and 0.5 $\mu$l of Advantage KlenTaq Polymerase Mix was prepared by using a PCR kit produced by Clontech Co., Advantage cDNA PCR Kit.

The reaction was performed under the following conditions.

The reaction mixture was kept at 94° C. for 2 minutes, and then subjected to a cycle of denaturation reaction at 98° C. for 30 seconds, annealing reaction at 60° C. for 30 seconds and extension reaction at 68° C. for 1 minute, which was repeated 30 times, and then final extension reaction was extended for 10 minutes. The reaction was stopped by cooling the reaction mixture to 4° C.

The obtained reaction product was separated by agarose gel electrophoresis, and fragments having a length expected from the nucleotide sequences of U1 and L1 were extracted from the gel and purified. The obtained fragments were directly cloned by using a vector kit for TA cloning, PGEM-T Vector System (Promega).

Inserted sequences were determined for a part of the obtained clones. As a result, 5 clones which had the target sequence were found among sequenced 32 clones.

The clone having the target sequence was used for the subsequent reaction. The same reaction mixture as mentioned above except that it contained about 5 ng of this plasmid and U2 and L2 instead of U1 and L1 was prepared, and a reaction product was obtained with the same reaction conditions as those mentioned above.

The obtained reaction product was separated by agarose gel electrophoresis, and fragments having a length expected from the nucleotide sequences of U1, U2, L1 and L2 were extracted from the gel and purified. The obtained fragments were directly cloned by using a vector kit for TA cloning, pGEM-T Vector System (Promega).

Inserted sequences were determined for a part of the obtained clones. As a result, clones having the nucleotide sequences shown in Table 2 were obtained. In Table 2, the target sequence is shown in the top line. The parenthesized numbers indicate designations of the clones, and a designation to which "*" is appended on the right side indicates a clone having a target sequence.

The clone having the target sequence was used for the subsequent reaction. The same reaction mixture as mentioned above was prepared except that it contained about 5 ng of this plasmid and U3 and L3 instead of U1 and L1, and a reaction product was obtained with the same reaction conditions as those mentioned above.

The obtained reaction product was separated by agarose gel electrophoresis, and fragments having a length expected from the nucleotide sequences of U1 to U3 and L1 to L3 were extracted from the gel and purified. The obtained fragments were directly cloned by using a vector kit for TA cloning, pGEM-T Vector System (Promega).

Inserted sequences were determined for a part of the obtained clones. As a result, 3 clones which had the target sequence were found among sequenced 27 clones. having the nucleotide sequences shown in Table 3 were obtained. In Table 3, the target sequence is shown in the top line. The parenthesized numbers indicate designations of the clones, and a designation to which "*" is added on the right side indicates a clone having a target sequence.

The clone having the target sequence was used for the subsequent reaction. The same reaction mixture as mentioned above was prepared except that it contained about 5 ng of this plasmid, and U4 and L4 instead of U1 and L1, and a reaction product was obtained with the same reaction conditions as those mentioned above.

The obtained reaction product was separated by agarose gel electrophoresis, and fragments having a length expected from the nucleotide sequences of U1 to U4 and L1 to L4 were extracted from the gel and purified. The obtained fragments were directly cloned by using a vector kit for TA cloning, pGEM-T Vector System (Promega).

Inserted sequences were determined for a part of the obtained clones. As a result, 5 clones which had the target sequence were found among sequenced 15 clones.

The clone having the target sequence was used for the subsequent reaction. The same reaction mixture as mentioned above was prepared except that it contained about 5 ng of this plasmid, and U5 and L5 instead of U1 and L1, and a reaction product was obtained with the same reaction conditions as those mentioned above.

The obtained reaction product was separated by agarose gel electrophoresis, and fragments having a length expected from the nucleotide sequences of U1 to U5 and L1 to L5 were extracted from the gel and purified. The obtained fragments were directly cloned by using a vector kit for TA cloning, PGEM-T vector System (Promega).

Inserted sequences were determined for a part of the obtained clones. As a result, 1 clones which had the target sequence were found among sequenced 19 clones.

In this way, DNA having a target sequence could be produced.

EXAMPLE 2

In order to synthesize DNA having the nucleotide sequence shown in SEQ ID NO: 12 (target sequence), oligomers having a length of 104 nucleotides, 1a, 1b, 2a, 2b, 3a, 3b, 4a and 4b were synthesized, each of which had each of the nucleotide sequences shown in SEQ ID NOS: 13–20. These oligomers correspond to Aa1, Aa2, Ab1, Ab2, Ba1, Ba2, Bb1 and Bb2, respectively, which are shown in the frame in FIG. 2.

Reaction mixtures having each of the compositions shown in Table 6 were prepared in four of tubes (Tube 1 to Tube 4), and PCR was performed by leaving at 94° C. for 1 minute, and repeating 30 times a cycle of reactions at 94° C. for 1 minute and 68° C. for 30 seconds. In this stage, a fragment of 179 bp is synthesized.

TABLE 6

Composition of reaction mixture (unit: $\mu$l)

|  | Tube 1 | Tube 2 | Tube 3 | Tube 4 |
|---|---|---|---|---|
| 10 × Pyrobest PCR reaction buffer | 10 | 10 | 10 | 10 |
| 2.5 mM dNTP mixture | 2 | 2 | 2 | 2 |
| Primer a (10 pmol/$\mu$l) | 4(1a) | 1(2a) | 4(3a) | 1(4a) |
| Primer b (10 pmol/$\mu$l) | 1(1b) | 4(2b) | 1(3b) | 4(4b) |
| Pyrobest DNA polymerase (5 unit/$\mu$l) | 0.5 | 0.5 | 0.5 | 0.5 |
| Water | 82.5 | 82.5 | 82.5 | 82.5 |
| Total | 100 | 100 | 100 | 100 |

After completion of the reaction, portions of 80 $\mu$l and 20 $\mu$l were taken out from Tube 1 and Tube 2, respectively, and mixed in a new tube (Tube 5). Similarly, portions of 20 $\mu$l and 80 $\mu$l were taken out from Tube 3 and Tube 4, respectively, and mixed in a new tube (Tube 6). The mixtures in Tube 5 and Tube 6 were allowed to react under the same conditions as described above. In this stage, a fragment of 326 bp is synthesized.

After completion of the reaction, portions of 50 $\mu$l and 50 $\mu$l were taken out from Tube 5 and Tube 6, respectively, and mixed in a new tube (Tube 7). The mixture in Tube 7 was allowed to react under the same conditions as described above. In this stage, a fragment of 612 bp is synthesized.

Then, the target fragment was amplified. Based on the sequences of the both ends of the target sequence, oligomers of 20-mer having the nucleotide sequences shown in SEQ ID NOS: 21 and 22, respectively, were prepared. These oligomers were used as primers (Upper and Lower), and a reaction mixture having the composition shown in Table 7 mentioned below was prepared (Tube 8). PCR was performed by leaving at 98° C. for 1 minute, and repeating 30 times a cycle of reactions at 98° C. for 30 seconds and 68° C. for 90 seconds.

TABLE 7

Composition of reaction mixture (unit: $\mu$l)

| 10 × Pyrobest PCR reaction buffer | 10 |
|---|---|
| Reaction product of Tube 7 | 4 |
| 2.5 mM dNTP mixture | 2 |
| Primer Upper (10 pmol/$\mu$l) | 5 |
| Primer Lower (10 pmol/$\mu$l) | 5 |
| Pyrobest DNA polymerase (5 unit/$\mu$l) | 0.5 |
| Water | 73.5 |
| Total | 100 |

Figure 3:
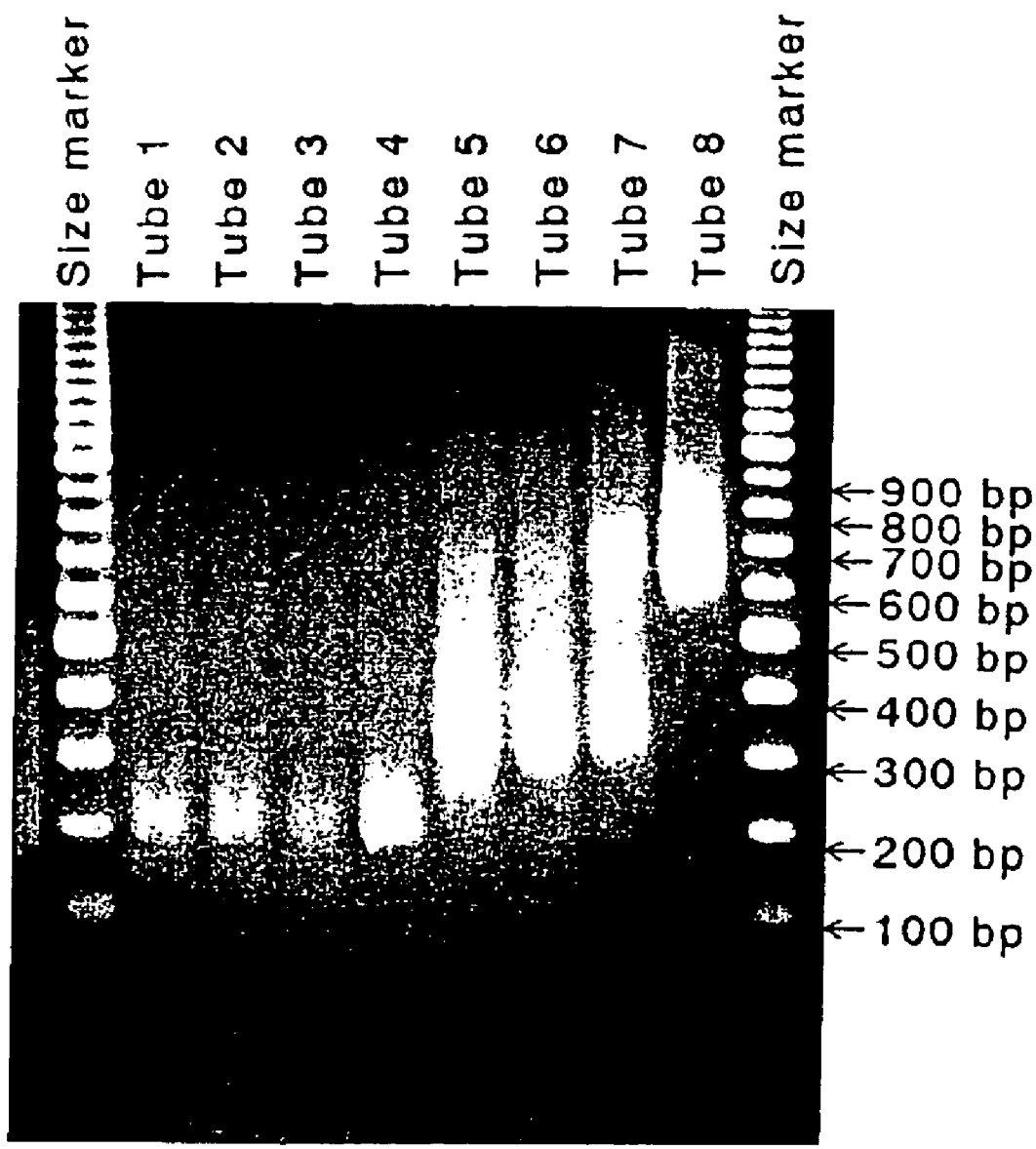
FIG. 3 shows results of electrophoretic analysis of the PCR products obtained in Example 2 (Tube 1 to Tube 8) (photograph of an electrophoretic image).

After the reaction described above, 5 $\mu$l each of the reaction products of Tube 1 to Tube 8 were subjected to agarose gel electrophoresis to confirm the amplification (FIG. 3). Since the amplification was confirmed, a target length of the reaction product obtained in Tube 8 was collected from the electrophoresis gel, and directly cloned by using PGEM-T Vector System (Promega).

Fifteen of the obtained clones were sequenced. As a result, one clone having the target sequence was obtained.

What is claimed is:

1. A method for producing DNA, which comprises the following steps (1) to (8):

(1) dividing a DNA target sequence which has a length of 1000 nucleotides or less into a 2N sections, wherein N is a positive integer greater than 1;

(2) designing partial sequences having a length of 80 to 150 nucleotides which comprise the sequences of each of one of the sections of step 1 and a part of a nucleotide sequence of an adjacent section or parts of nucleotide sequences of adjacent sections, wherein the part or parts have such a length that the nucleotide sequence of the each part can base pair with a nucleotide sequence complementary thereto;

(3) preparing oligomers comprising each of the 1st to Nth partial sequences of step (2) from the 5' end of the target sequence;

(4) preparing oligomers each comprising a nucleotide sequence complementary to each of the (N+1)th to (2N)th partial sequences from the 5' end of the target sequence;

(5) performing a polymerase chain reaction using the oligomer of step (3) having the Nth partial sequence from the 5' end of the target sequence and an oligomer of step (4) having a nucleotide sequence complementary to the (N+1)th partial sequence from the 5' end of the target sequence under conditions such that these oligomers act as primers and templates for a polymerase enzyme in the polymerase chain reaction;

(6) sequencing synthesized DNAs and (7) selecting DNA having a nucleotide sequence containing the Nth and (N+1)th partial sequences from the 5' end of the target sequence; and (8) repeating the following steps (8a) and (8b) and (8c) for successive J's, wherein J increases by a single integer, for each repetition, and wherein J is an integer, to be from 1 to N−1;

(8a) performing polymerase chain reaction by using the selected DNA, an oligomer having the (N−J)th partial sequence from the 5' end of the target sequence and an oligomer having a nucleotide sequence complementary to the (N+1+J)th partial sequence from the 5' end of the target sequence under such a condition that the DNA and oligomers should act as primers and templates; and (8b) sequencing synthesized DNAs, and (8c) selecting DNA having a nucleotide sequence containing the (N−J)th to (N+1+J)th partial sequences, thereby producing DNA having the target sequence.

* * * * *

UNITED STATES PATENT AND TRADEMARK OFFICE
CERTIFICATE OF CORRECTION

PATENT NO.   : 6,838,266 B2
DATED        : January 4, 2005
INVENTOR(S)  : Aotsuka, Satoshi It is certified that error appears in the above-identified patent and that said Letters Patent is hereby corrected as shown below:

<u>Title page,</u>
Item [56], References Cited, OTHER PUBLICATIONS,
"Horton, et al." reference, "vol. 77, pp. 81-88" should be changed to -- vol. 77, pp. 61-68 --.
*Assistant Examiner*, "Lori A. Chow" should be changed to -- Lori A. Clow --.

<u>Column 21,</u>
Line 54, "into a 2N sections" should be changed to -- into 2N sections --.

<u>Column 22,</u>
Line 62, "sequencing synthesized DNAs and" should be changed to -- sequencing synthesized DNAs; and --.
Line 67, "increases by a single integer," should be changed to -- increases by a single integer --.

<u>Column 24,</u>
Line 2, "primers and templates; and" should be changed to -- primers and templates, and --.

Signed and Sealed this

Thirteenth Day of December, 2005

JON W. DUDAS
*Director of the United States Patent and Trademark Office*